United States Patent [19]

Parker et al.

[11] 3,996,206

[45] Dec. 7, 1976

[54] PROCESS OF MAKING SUCROSE ESTERS

[75] Inventors: Kenneth John Parker, Oxted; Riaz Ahmed Khan, Sonning; Khizar Sultan Mufti, Reading, all of England

[73] Assignee: Tate & Lyle Limited, London, England

[22] Filed: Mar. 6, 1974

[21] Appl. No.: 448,695

[30] Foreign Application Priority Data

Mar. 16, 1973 United Kingdom ............ 12794/73

[52] U.S. Cl. ............................. 536/119 R; 252/356
[51] Int. Cl.$^2$ ......................................... C08B 37/00
[58] Field of Search ................. 260/234 R; 252/356

[56] References Cited

UNITED STATES PATENTS

| | | | |
|---|---|---|---|
| 3,251,827 | 5/1966 | Schnell et al. | 260/234 R |
| 3,480,616 | 11/1969 | Osipow et al. | 260/234 R |
| 3,558,597 | 1/1971 | Brachel et al. | 260/234 |
| 3,597,417 | 8/1971 | Myhre | 260/234 |

OTHER PUBLICATIONS

Morrison and Boyd, Organic Chemistry, Allyn and Bacon (1966) pp. 679–680.

*Primary Examiner*—Benjamin R. Padgett
*Assistant Examiner*—David Leland
*Attorney, Agent, or Firm*—Ostrolenk, Faber, Gerb & Soffen

[57] ABSTRACT

A surface active composition is prepared by reacting solid particulate sucrose with at least one triglyceride, in the presence of a basic transesterification catalyst, at a temperature of from 110° to 140° C, at atmospheric pressure and in the absence of any solvent. The preferred temperature range is 120° to 130° C, most preferably about 125° C. The preferred catalyst is potassium carbonate. The reaction can be accelerated by adding a suitable emulsifier, such as a diglyceride, a monoglyceride or a surfactant product of the reaction, to the reaction mixture.

15 Claims, No Drawings

PROCESS OF MAKING SUCROSE ESTERS

This invention relates to a surface active composition prepared by the transesterification of sucrose with one or more triglycerides.

Esters of sucrose with fatty acids, particularly the sucrose mono-esters and di-esters, are potentially very valuable as surfactants and have a number of unique advantages in this role. They are non-toxic, odourless and tasteless; they are non-irritating to the skin; and, when ingested, they hydrolyse to form normal food products. Unlike most surfactants, they are biodegradable under both aerobic and anaerobic conditions; and, unlike most other non-ionic surfactants, they are solid and thus readily usable in powdered or spray-dried products. detergents, are very good emulsifiers; and they perform well as detergents, either alone or in combination with anionic surfactants, and can be formulated either as high-foaming or low-foaming detergents. Accordingly, they can be used generally as domestic or industrial detergents, and also in specialized uses such as additives for foodstuffs, animal feeds, cosmetics, pharmaceuticals and agricultural chemicals. However, in spite of possessing these advantages, sucrose ester surfactants have never been exploited to their full potential because of difficulties arising in their production. Many processes have been proposed for the preparation of sucrose ester surfactants but, due to technical and economic disadvantages, it is still difficult to achieve large-scale industrial production at a price competitive with other surfactants.

Sucrose esters cannot be prepared by the direct esterification of sucrose with a fatty acid, but three other methods are possible: reaction with a fatty acid chloride; reaction with a fatty acid anhydride; and transesterification with a fatty acid ester. The reaction with acid chlorides, which is performed in the presence of pyridine, is uneconomical and will not give good yields of sucrose mono-esters or di-esters: it can be used to prepare sucrose octa-esters, but these are unsatisfactory as surfactants. Acid anhydrides of the higher fatty acids are not available commercially, and their preparation is complicated and expensive. Consequently, attempts at finding a commercial process for the preparation of sucrose ester surfactants have concentrated on the transesterification reaction, generally using methyl or glyceryl esters of fatty acids.

Most of the known transesterification processes are carried out in a solvent. The most commonly used solvent is dimethylformamide. The reaction is usually performed at about 90° C, in the presence of an alkaline catalyst (e.g. potassium carbonate), using the methyl ester of the fatty acid. It is necessary to remove all traces of water, by heating the system under reduced pressure as each component is added; and the methanol, or other alkanol, by-product of the transesterification must also be removed by prolonged heating of the reaction mixture under reduced pressure, so as to drive the reaction equilibrium in the desired direction. The critical need for anhydrous conditions, the prolonged heating under reduced pressure and, above all, the use of a solvent such as dimethylformamide are all serious disadvantages of this process; not only must the dimethylformamide be recovered for economic operation, but its residual presence can render the product toxic and smelly. It is generally necessary to employ a substantial excess of sucrose in the reaction, and this also has to be removed from the product.

In a modified form of the solvent transesterification process, sucrose is reacted with a methyl ester, such as methyl tallowate, in a solvent such as propylene glycol which dissolves the sucrose but not the fatty component. An emulsifying agent is used, and the reaction is performed in a so-called "micro-emulsion". Although this process avoids the disadvantages arising from the use of a toxic solvent such as dimethylformamide, it still employs an expensive solvent which has to be recovered, and it still has to be performed under reduced pressure and in the absence of any water.

A more recent modification of the solent transesterification process, described in British Patent Specification No. 1,332,190, uses water as the solvent. The sucrose is completely dissolved in water in the presence of a fatty acid soap, a fatty acid ester and a transesterification catalyst are added, and the mixture is dehydrated under reduced pressure and at elevated temperature so as to produce a homogeneous melt. The melt is then maintained at elevated temperature for the transesterification reaction to take place. Although this process avoids the problems which arise when using an organic solvent such as dimethylformamide or propylene glycol, it is a multi-stage process which still requires heating under reduced pressure, and the pressure must be carefully controlled in relation to the temperature when producing the dehydrated melt, in order to avoid hydrolysis of the fatty acid ester. The process is, therefore, undesirably complicated for use on an industrial scale.

A solvent-free transesterification process has also been proposed recently [vide J. Amer. Oil Chem. Soc. 1970, 47, (2), 56–60; and U.S. Pat. No. 3,714,144]. In accordance with this process, it is stated that the solvent-free transesterification must be carried out with the sucrose in the molten state; and the process is, therefore, performed at a temperature of from 170° to 190° C. After a short time, the molten sucrose begins to degrade to a black tarry mass, and the reaction with the fatty acid ester must necessarily be performed very quickly: the reaction is generally stopped within 20 minutes, and sometimes after only 2 minutes. As in the solvent processes, the reaction is performed under reduced pressure, to distill off the alcoholic by-product. Furthermore, the reaction must be performed in the presence of an alkali-free anhydrous soap, which serves to solubilize the fatty acid ester in the molten sucrose and to catalyse the transesterification: alkoxides, free alkalis and ordinary soaps are entirely unsatisfactory as catalyst in this process, and their presence results in very rapid decomposition of the sucrose and darkening of the reaction mixture. Thus, although this process avoids some of the disadvantages arising from the use of a solvent such as dimethylformamide, it has disadvantages of its own tending to make it unsatisfactory as a commercial-scale preparation for sucrose ester surfactants. Specifically, it is difficult to control, because the reaction must be completed very quickly to avoid degrading the triglycerides, it must still be performed under reduced pressure, and it requires the use of expensive special catalysts.

Contrary to all previous proposals, it has now surprisingly been discovered that sucrose ester surfactants can be prepared by the transesterification of sucrose with triglycerides, without using a solvent for any of the reactants, without performing the reaction in molten sucrose, without having to complete the reaction in a short time, without performing the reaction under reduced pressure, and without the use of a special type of catalyst. The invention thus provides a simple and cheap process for the preparation of sucrose ester surfactants, which does not require the use of special solvents or reagents or operation under difficult conditions such as a partial vacuum, thus overcoming the most serious technical and economic disadvantages of previous processes, and which is consequently eminently suitable for use on an industrial scale.

In accordance with the present invention, a surfactant is prepared by reacting solid particulate sucrose with at least one triglyceride in the presence of a basic transesterification catalyst, at a temperature in the range of from 110° to 140° C, at atmospheric pressure and in the absence of any solvent.

It will be appreciated that the process of the present cess of the invention, in terms of the fatty acids from which they are derived and the number of carbon atoms in the acid chains.

The triglyceride and sucrose are suitably used in substantially equimolar amounts, although the proportions are not critical. In the case of tallow, for example, the amount can be calculated on the basis of glyceryl tristearate. Other proportions can be used if it is desired to obtain a product containing a substantial amount of unreacted sucrose or triglyceride, for some special application, but generally no benefit is derived by using an excess of either reactant: indeed, it is an advantage of the present invention over previous processes that a substantial excess of sucrose need not be used, and consequently it is not necessary to remove excess sucrose from the product.

Table 1

| Triglyceride fat or oil | Caprylic C8 | Capric C10 | Lauric C12 | Myristic C14 | Myristoleic C14 | Pentadecanoic C15 | Palmitic C16 | Palmitoleic C16 | Margaric C17 | Stearic C18 | Oleic C18 | Linoleic C18 | Linolenic C18 | Ricinoleic C18 | Arachidic C20 | Eicosenoic C20 | Behenic C22 |
|---|---|---|---|---|---|---|---|---|---|---|---|---|---|---|---|---|---|
| Tallow | | | | 3.2 | 1.0 | 0.4 | 26.4 | 2.6 | 0.9 | 26.9 | 36.7 | (~1) | | | | | |
| Linseed | | | | | | | 6.3 | | | 4.3 | 18.2 | 14.3 | 56.7 | | | | |
| Cottonseed | | | | 0.6 | | | 21.7 | | | 2.1 | 17.8 | 57.9 | | | | | |
| Palm | | | | 0.9 | | | 46.6 | | | 4.1 | 39.3 | 9.1 | | | | | |
| Soybean | | | | | | | 10.5 | | | 3.8 | 23.7 | 55.5 | 6.6 | | | | |
| Groundnut | | | | | | | 9.0 | | | 3.5 | 64.5 | 18.2 | | | 1.2 | (0.9?) | (1.6?) |
| Coconut | 8.0 | 6.7 | 51.3 | 16.2 | | | 7.6 | | | 2.7 | 5.9 | 1.6 | | | | | |
| Castor | | | | | | | 0.9 | | | | 9.6 | 10.3 | | 79.0 | | | | invention is completely different from the previous ones, in that it uses a heterogeneous reaction mixture wherein the solid particulate sucrose is suspended in the triglyceride, whereas the previous processes aimed at achieving a homogeneous system by either dissolving or melting the sucrose. In view of the methods used in the prior art processes, it is very surprising to find that an effective surfactant material, containing a substantial proportion of the desirable sucrose mono-ester, can be obtained without the use of a solvent and without melting the sucrose, at atmospheric pressure, under the conditions of the present invention.

One or more triglycerides of fatty acids having at least 8 carbon atoms, preferably at least 12 and most preferably from 16 to 18 carbon atoms, may be used in the process of the invention. It is normally convenient to use naturally occurring mixtures of triglycerides. Both for economic reasons and because it yields a particularly effective surfactant product, the most highly preferred natural triglyceride is tallow, which contains glyceryl esters of stearic, palmitic and oleic acids; but other triglyceride fats and oils can be used, for example, lard, palm oil, cottonseed oil, soybean oil, olive oil, groundnut oil, coconut oil, castor oil and linseed oil. However, it is generally less desirable to use triglycerides derived from highly unsaturated fatty acids, for example, the so-called "drying oils" such as linseed oil, because they tend to oxidize and become discoloured during the process of the invention, and the product has relatively inferior surfactant properties: in general, it is preferred to use triglycerides derived from acids containing not more than one double bond. The presence of hydroxyl groups in the acid chain can also be detrimental to the surfactant properties of the product. Table 1 shows the composition of some examples of triglyceride fats and oils which can be used in the process of the invention, in terms of the fatty acids from The catalyst used in the process of the invention may be any of the basic compounds conventionally used as transesterification catalysts, but potassium carbonate and sodium methoxide are found to give particularly good results. Other basic compounds, such as tertiary or quaternary organic bases, silicates and borates may also be used. If desired, a mixture of such compounds may be employed. The catalyst concentration is not critical, but it is generally desirable to use at least 2% of catalyst in order to attain a satisfactory rate of reaction and thus produce a surfactant material within a reasonably short time. The reaction can be accelerated by using higher concentrations of catalyst, and optimum results are generally obtained at concentrations of 5–12 percent, preferably about 10 percent. In general, no additional benefit is derived by further raising the catalyst concentration, and levels of above 20 percent are not likely to be used in practice. (All these percentage concentrations are by weight, on the basis of the weight of the reaction mixture).

In carrying out the process of the invention, the triglyceride is first melted if it is a solid such as tallow. In accordance with one embodiment, the sucrose and the basic catalyst are then added, and the resulting suspension is heated with stirring, to bring about the transesterification reaction. Alternatively, the triglyceride can first be heated with the catalyst alone, so that it is partly saponified, and the sucrose then added to the reaction mixture for the transesterification to take place. However, this preliminary saponification step is generally unnecessary when using an emulsifier, in accordance with the preferred embodiment of the invention described hereinafter.

Although no solvent is used in the process of the invention, the reaction is performed at a temperature well below the melting point of sucrose, in the range of from 110° to 140° C. The preferred temperature range is from 120° to 130° C, and the reaction is most preferably performed at about 125° C. (All these values refer to the internal temperature of the reaction mixture). Substantially no reaction takes place at temperatures below 110° C, while at temperatures above 140° C charring occurs and the product does not have satisfactory surfactant properties. The reaction mixture can be maintained at the desired temperature by any conventional means allowing adequate heat transfer and temperature control, for example, by providing the reaction vessel with an external jacket through which steam is passed. In some cases, especially if violent agitation is applied to the reaction mixture, it may be necessary to cool the mixture during the course of the reaction so as to maintain the required temperature, for example, by passing water through the external jacket. The process is carried out at atmospheric pressure, without distilling off any of the components: for example, it can be carried out in a simple open reaction vessel provided with suitable heating and stirring means. A conventional type of motor-driven stirrer may be used; but in order to provide adequate mixing and keep the temperature constant throughout the reaction mixture, especially in a large vessel, it is sometimes desirable to use a high-shear mixer driven at several thousand revolutions per minute.

The sucrose used in the process of the invention is normally in the form of particulate refined sugar, such as granulated sugar. The sucrose particle size is not critical, but particles which are too large can be difficult to disperse adequately in the reaction mixture, and it is therefore generally preferred to use sucrose of a particle size smaller than 250 microns. The sucrose can be ground and sieved before use, so as to obtain the desired particle size, but this is unnecessary if a high-shear mixer is being used to agitate the reaction mixture, since such a mixer will immediately comminute the sucrose particles.

Unlike the transesterification processes using an organic solvent, the process of the present invention does not require dehydration of the reactants, and the traces of water normally present in the starting materials are not detrimental. On the other hand, the process of the invention does not use water as a reaction solvent, and its presence at levels in excess of about 1 percent by weight tends to be detrimental, because the reaction slows down, the sucrose tends to form large lumps, and soap formation rapidly occurs.

The duration of the reaction depends upon the nature of the triglyceride, the amount and type of catalyst, the efficiency of mixing, and the reaction temperature used. There is an initiation period, generally lasting at least one hour and possibly several hours, depending upon the reaction conditions. The mixture becomes more viscous as the reaction proceeds, and the reaction is terminated when the mixture becomes too viscous for adequate stirring. Under optimum reaction conditions, the reaction can be finished in as little as 6 hours, but is sometimes continued for 14–16 hours, or even longer, in order to obtain optimum yields of surfactant. The progress of the reaction can be followed, for example, by subjecting samples of the reaction mixture to chromatography at appropriate time intervals.

In accordance with a preferred embodiment of the invention, it is found that the initiation period and the overall reaction time can be substantially reduced by adding an emulsifier to the reaction mixture. The most effective additive so for discovered is the surfactant product itself, and this is suitably added at a concentration of 5–10 percent by weight, based on the total weight of the reaction mixture. Other effective emulsifiers, which may be added in similar quantities, are diglycerides and monoglycerides, the former being more effective than the latter. Soaps such as sodium stearate are found to be less effective for this purpose. It is theorized that these additives behave as solid/liquid emulsifying agents in the heterogeneous reaction system, and thus act as physical catalysts for the process of the invention. Thus the reaction between sucrose and a pure triglyceride, such as glycerol trioleate, occurs very slowly and has a long initiation period because, it is believed, some lower glyceride must be formed from the triglyceride before the transesterification can proceed. If a small portion of the surfactant product, or of a diglyceride or monoglyceride, is added to the reaction mixture, the reaction time is considerably shortened. Natural triglyceride fats and oils, such as tallow, contain some diglyceride or monoglyceride and thus react faster than the pure triglycerides, but the reaction time can still be substantially shortened by the addition of the aforementioned emulsifiers.

The product of the reaction, comprising a mixture of compounds, can be used directly as a biodegradable, non-toxic surfactant, without any purification; although, if desired, the sucrose esters in the product can be separated and purified by conventional techniques, such as chromatography, a large proportion being made up of the sucrose mono-esters which are particularly valuable as surfactants. The product of the reaction solidifies when it cools and it can then be formulated into various compositions: for example, it can be formulated with the conventional extenders and adjuvants, to produce detergent powder compositions. Compositions for other purposes, such as cosmetics, foodstuffs and agricultural chemicals, can be formulated in the conventional manner. Since no solvent is used in the process of the invention, the costly and complicated steps of solvent recovery and product purification are completely avoided.

The performance as a detergent of the product of the invention, such as that prepared in Example 1 or Example 15 hereinafter, has been assessed by means of standardized washing procedures, and it has been found to be at least as effective as sodium dodecylbenzene sulphonate, which is a standard surfactant used in the formulation of conventional detergents.

The invention is illustrated by the following Examples, in which all percentages are given by weight.

EXAMPLE 1

Reaction of Sucrose with Tallow in the presence of Potassium Carbonate at 125° C A surfactant was prepared by reacting the following materials:

| Tallow | 40.0 g | (64.5%) |
|---|---|---|
| Sucrose | 17.0 g | (27.4%) |
| $K_2CO_3$ | 5.0 g | (8.1%). |

The tallow was melted in a 250 ml beaker which was immersed in an oil bath maintained at a constant temperature of 125° C. When the temperature of the tallow reached 125° C, the sucrose (having a particle size of less than 250 microns) and anhydrous potassium carbonate were added. The suspension was kept mixed by means of a 5 cm diameter four-blade inclined paddle, which was rotated by an electric motor at between 400 and 1,200 r.p.m., depending on the viscosity of the mixture. After about 2 hours, the initiation of the reaction was indicated by considerable foaming, and the mixture started to thicken. The foaming subsided after approximately 5 hours, and the mixture continued to thicken as the reaction proceeded. The mixing was stopped after about 9 hours, and the reaction product was allowed to cool and solidify, yielding 61.0 g of a cream-coloured waxy surfactant material having good oil-dispersing properties.

The results of chromatographic analysis of the reaction mixture at various times during the reaction are shown in Table 2.

Table 2

| Time in Hours | Triglycerides (%) | Diglycerides (%) | Monoglycerides (%) | Sucrose (%) | Sucrose Monoesters (%) |
|---|---|---|---|---|---|
| 0 | 64.5 | — | — | 27.4 | — |
| 3 | 62.2 | & 3 | — | 24.4 | — |
| 4 | 40.8 | 10.8 | & 3.7 | 22.0 | — |
| 5 | 27.2 | 12.5 | 5.8 | 18.6 | & 5.2 |
| 6 | 19.0 | 19.6 | 11.9 | 15.0 | 16.0 |
| 7 | 14.9 | 17.5 | 15.1 | 12.9 | 17.3 |
| 8 | 12.0 | 12.5 | 14.4 | 11.5 | 22.5 |
| 9 | 10.6 | 9.7 | 14.8 | 11.3 | 24.7 |

EXAMPLE 2

Reaction of Sucrose with Tallow in the presence of Potassium Carbonate at 115° C The procedure of Example 1 was repeated, except that the reaction was conducted at 115° C. The initiation of the reaction was indicated by a thickening of the reaction mixture after about 13 hours, and the mixing was stopped after about 22 hours. The reaction mixture was then allowed to cool and solidify, yielding a surfactant product similar to that obtained in Example 1.

The results of chromatographic analysis of the reaction mixture at various time during the reaction are shown in Table 3.

Table 3

| Time in Hours | Triglycerides (%) | Diglycerides (%) | Monoglycerides (%) | Sucrose (%) | Sucrose Monoesters (%) |
|---|---|---|---|---|---|
| 0 | 64.5 | — | — | 27.4 | — |
| 9 | 64.5 | 5.7 | — | 27.3 | — |
| 12 | — | 9.6 | & 0.7 | 28.0 | — |
| 14 | 50.2 | 8.3 | 1.7 | 26.1 | — |
| 16 | 21.5 | 9.3 | 6.1 | 20.7 | & 4.8 |
| 18 | — | 8.4 | 11.0 | 19.8 | 12.0 |
| 20 | 20.5 | 5.7 | 10.5 | 16.3 | 10.2 |
| 22 | 15.4 | 4.6 | 12.0 | 17.3 | 12.4 |

EXAMPLE 3

Reaction of Sucrose with Tallow in the presence of Potassium Carbonate at 135° C The procedure of Example 1 was repeated, except that the reaction was performed at 135° C. The initiation time for the reaction was reduced to just over 1 hour, and the mixing was stopped after about 7 hours. The reaction product was allowed to cool and solidify, yielding a surfactant similar to that produced in Example 1, except for being darker in colour.

The results of chromatographic analysis of the reaction mixture at various times during the reaction are shown in Table 4.

Table 4

| Time in Hours | Triglycerides (%) | Diglycerides (%) | Monoglycerides (%) | Sucrose (%) | Sucrose Monoesters (%) |
|---|---|---|---|---|---|
| 0 | 64.5 | — | — | 27.4 | — |
| 1 | 60.4 | 3.8 | 1.2 | 27.3 | — |
| 2 | 45.7 | 18.4 | 3.4 | 25.9 | — |
| 3 | 32.8 | 5.6 | 7.1 | 24.4 | 6.4 |
| 4 | 10.9 | 3.9 | 11.9 | 14.9 | 11.8 |
| 5 | — | 3.0 | 15.1 | 13.7 | 18.6 |
| 6 | 9.6 | 2.6 | 10.4 | 13.5 | 10.0 |
| 7 | — | 3.0 | 10.5 | 13.6 | 10.8 |

EXAMPLE 4

This Example illustrates the effects of using the potassium carbonate transesterification catalyst at higher concentrations.

The procedure of Example 1 was repeated, except that the starting materials were used in the following amounts:

| Tallow | 40.0 g | (62.0%) |
| Sucrose | 17.0 g | (26.4%) |

-continued

| | | |
|---|---|---|
| K$_2$CO$_3$ | 7.5 g | (11.6%) |

The resulting product had a high sucrose monoester concentration and a low tallow content, with a good colour and good detergent properties.

The results of chromatographic analysis of the reaction mixture at various times are shown in Table 5.

Table 5

| Time in Hours | Triglycerides (%) | Diglycerides (%) | Monoglycerides (%) | Sucrose Monoesters (%) |
|---|---|---|---|---|
| 0 | 62.0 | — | — | — |
| 1 | 45.4 | 16.8 | — | — |
| 2 | — | 20.0 | — | — |
| 3 | 35.2 | 20.2 | 0.4 | — |
| 4 | 26.6 | 17.7 | 2.1 | — |
| 5 | — | 20.3 | 4.7 | — |
| 6 | 7.6 | 15.9 | 6.8 | 5.3 |
| 7 | 4.7 | 11.3 | 10.4 | 10.9 |
| 9 | — | 5.3 | 14.5 | 39.4 |

EXAMPLE 5

Reaction of Sucrose with Glycerol Trioleate in the presence of Potassium Carbonate This Example illustrates the effects of using a pure tiglyceride, instead of a natural fat or oil, in the reaction.

The procedure of Example 1 was repeated, except that the 40.0 g of tallow were replaced by 40.0 g of reagent-grade glycerol trioleate. The reaction was much slower than in Example 1, requiring an initiation period of 6–7 hours and an overall reaction time of about 16 hours, though the end product was similar to that obtained in Example 1.

The results of chromatographic analysis of the reaction mixture at various times are shown in Table 6.

Table 6

| Time in Hours | Trioleate (%) | Dioleate (%) | Sucrose Monoesters (%) |
|---|---|---|---|
| 0 | 64.5 | — | — |
| 6 | 64.2 | — | — |
| 8 | 29.7 | 10.7 | — |
| 10 | 12.0 | 24.1 | 4.0 |
| 11 | — | 18.9 | 19.3 |
| 14 | — | 6.6 | 22.0 |
| 15 | 4.6 | 7.6 | 27.2 |

EXAMPLE 6

Reaction of Sucrose with Glycerol Trioleate in the presence of Potassium Carbonate and added Surfactant This Example illustrates how the reaction between sucrose and a pure triglyceride is accelerated by the presence of a small proportion of the sucrose surfactant product of Example 1 in the initial reaction mixture.

The procedure of Example 5 was repeated, except that 4.0 g of the glycerol trioleate were replaced by the same amount of the surfactant product, so that the initial reaction mixture had the following composition:

| | | |
|---|---|---|
| Glycerol trioleate | 36.0 g | (58.06%) |
| Surfactant product | 4.0 g | (6.45%) |
| Sucrose | 17.0 g | (27.42%) |
| K$_2$CO$_3$ | 5.0 g | (8.06%) |

The reaction had an initiation time of about 1 hour and was completed in about 8 hours, yielding a surfactant product with good detergent properties.

The results of chromatographic analysis of the reaction mixture at various times are shown in Table 7.

Table 7

| Time in Hours | Trioleate (%) | Dioleate (%) | Sucrose Monoester (%) |
|---|---|---|---|
| 0 | 58.06 | — | — |
| 1 | & — | — | — |
| 2 | & 34.0 | & 19.3 | — |
| 3 | 12.5 | 12.2 | — |
| 4 | 10.2 | 16.0 | & 5.3 |
| 5 | 11.6 | 20.2 | 16.6 |
| 6 | 8.0 | 12.6 | 18.9 |
| 7 | 3.2 | 10.2 | 20.3 |
| 8 | 3.1 | 9.5 | 22.6 |

EXAMPLE 7

Reaction of Sucrose with Glycerol Trioleate in the presence of Potassium Carbonate and Glycerol Dioleate This Example illustrates how the reaction between sucrose and a pure triglyceride can be accelerated by conducting the reaction in the presence of a small amount of diglyceride.

The procedure of Example 5 was repeated, except that 4.0 g of the glycerol trioleate were replaced by the same amount of glycerol dioleate, so that the initial reaction mixture had the following composition:

| | | |
|---|---|---|
| Glycerol trioleate | 36.0 g | (58.06%) |
| Glycerol dioleate | 4.0 g | (6.45%) |
| Sucrose | 17.0 g | (27.42%) |
| K$_2$CO$_3$ | 5.0 g | (8.06%) |

The initiation time of the reaction was about 3 hours, and the reaction was completed in about 10 hours, giving a surfactant product with good detergent properties. Thus, the dioleate was effective in reducing the reaction time, though not as effective as the surfactant product used in Example 6.

The results of chromatographic analysis of the reaction mixture at various times are shown in Table 8.

Table 8

| Time in Hours | Trioleate (%) | Dioleate (%) | Sucrose Monoesters (%) |
|---|---|---|---|
| 0 | 58.06 | 6.45 | — |
| 1 | — | — | — |
| 2 | 37.9 | — | — |
| 3 | 27.8 | 18.6 | — |
| 4 | 15.1 | 14.3 | 8.6 |
| 5 | — | 21.9 | 18.6 |
| 6 | 6.8 | 12.3 | 22.5 |
| 7 | — | 14.2 | 28.0 |
| 8 | 5.2 | 19.6 | 21.5 |
| 9 | 4.3 | 9.1 | 23.8 |
| 10 | — | 7.8 | 24.2 |

EXAMPLE 8

Reaction of Sucrose with Glycerol Trioleate in the presence of Potassium Carbonate and Glycerol Mono-oleate This Example illustrates how the reaction between sucrose and a pure triglyceride can be accelerated by adding small proportion of monoglyceride to the initial reaction mixture.

The procedure of Example 5 was repeated, except that 4.0 g of the glycerol trioleate was replaced by the same amount of glycerol mono-oleate, so that the initial reaction mixture had the following composition:

| | | |
|---|---|---|
| Glycerol trioleate | 36.0 g | (58.06%) |
| Glycerol mono-oleate | 4.0 g | (6.45%) |
| Sucrose | 17.0 g | (27.42%) |
| $K_2CO_3$ | 5.0 g | (8.06%) |

The reaction took about 12 hours to complete, yielding a surfactant product having good detergent properties. Thus, although the mono-oleate is effective in accelerating the reaction of the pure trioleate, it is not as effective as the dioleate or the surfactant product in this respect.

The results of chromatographic analysis of the reaction mixture at various times are shown in Table 9.

Table 9

| Time in Hours | Trioleate (%) | Dioleate (%) | Sucrose Monoesters (%) |
|---|---|---|---|
| 0 | 58.06 | — | — |
| 2 | 27.4 | & 18.5 — | — |
| 4 | 28.9 | 19.5 | — |
| 6 | 28.6 | 13.3 | — |
| 8 | 23.9 | 20.7 | & 19.7 |
| 9 | 6.5 | 19.5 | 26.1 |
| 10 | 3.6 | 12.5 | 30.2 |
| 11 | & — | & — | & — |
| 12 | — | & 7.6 | & 32.2 |

EXAMPLE 9

Reaction of Sucrose with Cottonseed Oil

The procedure of Example 1 was repeated, except that the 40.0 g of tallow were replaced by 40.0 g of cottonseed oil. The mixing was stopped after 11.5 hours, and the product was allowed to cool and solidify, yielding 61.0 g of a light-brown waxy surfactant material possessing good oil-dispersing properties.

EXAMPLE 10

Reaction of Sucrose with Palm Oil

The procedure of Example 1 was repeated, except that the 40.0 g of tallow were replaced by 40.0 g of crude Malayan palm oil. The mixing was stopped after 10 hours, and the product was allowed to cool and solidify, yielding 61.0 g of a pale cream waxy surfactant material having good oil-dispersing properties.

EXAMPLE 11

Reaction of Sucrose with Linseed Oil

The procedure of Example 1 was repeated, except that the 40.0 g of tallow were replaced by 40.0 g of linseed oil. The mixing was stopped after 9 hours, and the product was allowed to cool and solidify, yielding 61.0 g of a dark brown waxy surfactant material. The product had inferior oil-dispersing properties, as compared with those of the product of Example 1, due to the high degree of unsaturation in the linseed oil.

EXAMPLE 12

Reaction of Sucrose with Castor Oil

The procedure of Example 1 was repeated, except that the 40.0 g of tallow were replaced by 40.0 g of castor oil. The mixing was stopped after 10.5 hours, and the product was allowed to cool, yielding 61.0 g of a sticky surfactant material. The oil-dispersing properties of this product were not as good as those of the product of Example 1.

EXAMPLE 13

Reaction of Sucrose with Groundnut Oil

The procedure of Example 1 was repeated, except that the 40.0 g of tallow were replaced by 40.0 g of groundnut oil. The mixing was stopped after 9 hours, and the product was allowed to cool and solidify, yielding 61.0 g of a pale cream waxy surfactant material having good oil-dispersing properties.

EXAMPLE 14

Reaction of Sucrose with Coconut Oil

The procedure of Example 1 was repeated, except that the 40.0 g of tallow were replaced by 26.7 g of coconut oil. The mixing was stopped after 12 hours, and the product was allowed to cool and solidify, yielding 47.0 g of a pale cream waxy surfactant material possessing adequate oil-dispersing properties.

EXAMPLE 15

Large-scale Reaction of Sucrose with Tallow 76.19 kg of tallow were melted in a 200 liter reactor which was heated by passing steam through an external jacket. When the temperature of the tallow reached 125° C, 32.38 kg of sucrose (having a particle size smaller than 250 microns) and 9.52 kg of anhydrous potassium carbonate were added. The resulting suspension was kept mixed by means of a 30 cm propeller driven at 400 r.p.m. by a threequarter horse-power motor, while maintaining its temperature at 125° C. The mixture started to foam after 13 hours; and it was then mixed for a further 23 hours at 125° C, during which time the foam subsided, and the mixture turned dark brown and became considerably more viscous. The product was then allowed to cool and solidify, yielding 112.3 kg of a brown waxy surfactant material having good detergent properties.

EXAMPLE 16

Large-scale Reaction of Sucrose with Tallow

This Example illustrates how the reaction initiation time can be reduced by adding a small proportion of the surfactant product to the initial mixture.

50.79 kg of tallow and 6.0 kg of the surfactant product from Example 15 were melted and mixed in the same apparatus as used in Example 15. When the temperature of the mixture reached 125° C, 21.59 kg of sucrose (having a particle size of less than 250 microns) and 6.35 kg of anhydrous potassium carbonate were added, and the resulting suspension was kept mixed at 125° C. Considerable foaming of the mixture occurred after 6 hours, and the mixing was then continued for a further 24 hours, still maintaining the temperature at 125° C. The product was then allowed to cool and solidify, yielding 80.9 kg of a brown waxy surfactant material having good detergent properties.

EXAMPLE 17

Large-scale Reaction of Sucrose with Tallow

This Example illustrates how the reaction time can be further reduced by subjecting the reaction mixture to high-shear agitation, as well as using a small proportion of the surfacant product in the initial mixture.

50.79 kg of tallow and 6.0 kg of the surfactant product of Example 15 were mixed in a 200 liter reactor, using a four horse-power Silverson mixer fitted with a high-shear head and operating at 3,000 r.p.m., while passing steam through an external jacket fitted to the reactor. When the temperature of the resulting suspension reached 125° C, 21.59 kg of sucrose (granulated sugar) and 6.35 kg of anhydrous potassium carbonate were added, and the mixing was continued. The reaction mixture began to thicken after 1.5 hours, and after about 5 hours cooling water was circulated through the jacket around the reactor, in order to maintain the temperature of the mixture at 125° C. The mixing was stopped after 9 hours, and the reaction product was allowed to cool and solidify, yielding 80.9 kg of a light-brown waxy surfactant material having good detergent properties.

COMPARATIVE EXAMPLE 1

Reaction of Sucrose with Tallow in the presence of Potassium Carbonate at 105° C.

The procedure of Example 1 was repeated, except that the reaction was conducted at 105° C. The initiation of the reaction took 22 hours, and practically no product had been formed even after 30 hours. The reaction was discontinued at this point. The resulting mixture did not have any useful surfactant properties.

COMPARATIVE EXAMPLE 2

Reaction of Sucrose with Tallow in the presence of Potassium Carbonate at 145° C The procedure of Example 1 was repeated, except that the reaction was conducted at 145° C. The reaction mixture began to char almost immediately, and the process had to be discontinued after 2 hours, becuase the mixture had become carbonized into a black mass. The resulting mixture did not have any useful surfactant properties.

We claim:

1. A process for preparing a surfactant, which comprises reacting solid particulate sucrose with at least one triglyceride in the presence of a basic transesterification catalyst, at a temperature in the range of from 110° to 140° C, at atmospheric pressure without distilling off any of the components, and in the absence of any solvent.

2. A process according to claim 1, wherein the reaction is performed at a temperature in the range of from 120° to 130° C.

3. A process according to claim 1, wherein the reaction is performed at a temperature of about 125° C.

4. A process according to claim 1, wherein there is used at least one triglyceride of a fatty acid having from 16 to 18 carbon atoms.

5. A process according to claim 1, wherein said triglyceride is tallow.

6. A process according to claim 1, wherein said triglyceride and sucrose are used in substantially equimolar amounts.

7. A process according to claim 1, wherein said catalyst is potassium carbonate.

8. A process according to claim 1, wherein the catalyst is used at a concentration in the range of from 5 to 12 percent by weight.

9. A process for preparing a surfactant, which comprises reacting solid particulate sucrose with at least one triglyceride, in the presence of a basic transesterification catalyst and of an emulsifier for the sucrose and triglyceride, at a temperature of from 110° to 140° C, at atmospheric pressure without distilling of any of the components, and in the absence of any solvent.

10. A process according to claim 9, wherein said emulsifier is selected from the group consisting of diglycerides, monoglycerides and the surfactant products of the reaction.

11. A process according to claim 9, wherein the reaction is performed at a temperature of from 120° to 130° C.

12. A process according to claim 9, wherein said emulsifier is used at a concentration in the range of from 5 to 10 percent by weight.

13. A process according to claim 9, wherein said solid particulate sucrose has a particle size smaller than 250 microns.

14. A process according to claim 13, wherein said triglyceride is tallow, said triglyceride and sucrose are used in substantially equimolar amounts, said catalyst is potassium carbonate, said catalyst is used at a concentration from 5 to 12 percent by weight, said temperature is about 125° C. and said emulsifier is used at a concentration in the range of from 5 to 10 percent by weight.

15. A process according to claim 1, wherein said solid particulate sucrose has a particle size smaller than 250 microns.

* * * * *